(12) United States Patent
Kober et al.

(10) Patent No.: US 6,753,003 B1
(45) Date of Patent: Jun. 22, 2004

(54) DITHIOCARBAMATE LIQUID FORMULATIONS

(75) Inventors: Reiner Kober, Fusseönheim (DE); Thomas Kröhl, Mainz (DE); Günter Oetter, Frankenthal (DE); Oliver Borzyk, Speyer (DE); Karl-Friedrich Jäger, Limburgerhof (DE); Olivier Grosjean, Mannheim (DE); Hans-Michael Fricke, Limburgerhof (DE); Sergi Vizoso-Sansano, Limburgerhof (DE); Hans Ziegler, Mutterstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 44 days.

(21) Appl. No.: 09/979,980

(22) PCT Filed: May 29, 2000

(86) PCT No.: PCT/EP00/04887

§ 371 (c)(1), (2), (4) Date: Nov. 29, 2001

(87) PCT Pub. No.: WO00/72681

PCT Pub. Date: Dec. 7, 2000

(30) Foreign Application Priority Data

May 31, 1999  (DE) .......................... 199 24 981

(51) Int. Cl.$^7$ .......................... A01N 25/00; A01K 9/00
(52) U.S. Cl. ...................... 424/405; 424/400
(58) Field of Search .................. 424/400, 405; 504/116, 189, 313; 514/483, 477

(56) References Cited

U.S. PATENT DOCUMENTS

| | | | |
|---|---|---|---|
| 3,131,119 A | 4/1964 | Fordyce | 167/23 |
| 3,773,926 A | 11/1973 | Knowles et al. | 424/78 |
| 4,824,864 A | 4/1989 | Fischer et al. | 514/494 |
| 6,087,305 A | * 7/2000 | Kober et al. | 504/313 |

FOREIGN PATENT DOCUMENTS

| | | |
|---|---|---|
| DE | 33 38 979 | 5/1985 |
| DE | 34 26 078 | 1/1986 |
| EP | 243 872 | 11/1987 |
| EP | 0 243 872 A1 * | 11/1987 |
| EP | 0 245 970 | 11/1987 |
| EP | 0 245 970 A1 * | 11/1987 |
| EP | 435 760 | 7/1991 |
| EP | 460 612 | 12/1991 |
| EP | 0 544 518 A1 * | 6/1993 |
| EP | 568 378 | 11/1993 |
| EP | 0 697 171 | 2/1996 |
| EP | 0 875 142 | 11/1998 |
| GB | 903382 | 8/1962 |
| GB | 2 119 652 | 11/1983 |
| GB | 2 119 652 A2 * | 11/1983 |
| RO | 68170 | 11/1979 |
| ZA | 6804521 | 2/1968 |

* cited by examiner

*Primary Examiner*—Thurman K. Page
*Assistant Examiner*—S. Tran
(74) *Attorney, Agent, or Firm*—Keil & Weinkauf

(57) ABSTRACT

An essentially anhydrous dithiocarbamate liquid formulation comprises:

a) 10 to 70% by weight of at least one active ingredient from the class of the dithiocarbamates,
b) 10 to 89% by weight of an essentially anhydrous oil phase,
c) 1 to 40% by weight of a polyhydroxystearic acid or a derivative thereof and/or an alkyl or alkenyl glycerin ether ethoxylate,
d) 0 to 40% by weight of at least one anionic surfactant.

13 Claims, No Drawings

DITHIOCARBAMATE LIQUID FORMULATIONS

The invention essentially relates to anhydrous liquid formulations with active ingredients from the class of the dithiocarbamates, in particular metiram. "Essentially anhydrous" means for the purposes of the present invention that the water content is 0 to 5% by weight, in particular 0.1 to 2.5% by weight, and advantageously 0.1 to 1% by weight (in each case based on the total weight of the liquid formulation).

Thiocarbamates, dithiocarbamates, and EBTCs (ethylenebisthiocarbamates) and EBDCs (ethylenebisdithiocarbamates) are generally known as fungicidal active ingredients, in particular as contact fungicides or biocides. Specifically, they are active ingredients such as, for example, metiram, mancozeb, maneb, nabam or else the N,N-dimethylthiocarbamates thiram or ziram.

However, a particular problem of these active ingredients is their relatively high instability. This is caused by the low stability of the C-S and S-S bonds and of the thiocarbamate function, in particular at low pH values and to nucleophilic agents.

A possibility for stable formulations for crop protection is to process the materials as solid formulations. Solid powder formulations which are known are, for example, Manzate 200 75 WG (product of DuPont), Polyram DF (product of BASF AG) and Vondozeb 75 WG (product of Elf Atochem).

DE-A 33 38 979 discloses the stabilization of polyethylenethiuram disulfides by means of formaldehyde or paraformaldehyde. Moreover, DE-A 34 26 078 describes the stabilization of, for example, Zineb by means of calcium oxide. Also, EP-A 0 568 378 discloses the use of EBDC formulations in the form of aqueous granules with improved flowability.

In such formulations, the undesired degradation product by-product ethylene thiourea (ETU) needs careful consideration, owing to its high toxicity. It is important to lower the ETU content under defined threshold values by stabilization measures, for example using hydroxymethane sulfinate (HMS) or a salt thereof, see EP-A-460 612.

In many cases, liquid products are preferred nowadays to the abovementioned solid. formulations. The liquid products have the advantage that they show good miscibility with oily tankmix additives, such as, for example, the so-called Spraytex oil, a paraffin derivative (product of Exxon) for a water/oil or pure oil application, even under ULV (ultra-low volume) conditions; see EP-A-435 760 and EP-A 697 171.

Such ULV conditions, or ULV oil/water mixtures, are particularly important for aerial application. Using aircraft, it is possible to apply relatively low application rates per hectare, approximately 10 to 30 l of the fungicidal active ingredient or of the corresponding formulation, in such a fashion that the effect is reliable and drift is low. Target crops which are typically suitable for such an aerial application of EBDCs are, in particular, bananas and coffee. Aerial application, or ULV application, is done for virtually all banana plantations.

In such an application, it is in particular the so-called oil SC variants (SC=suspension concentrate) of the formulations which are advantageous since they are generally distinguished in the tankmix by good miscibility with spray oils. The oil component improves the rainfastness upon use of the formulations during the tropical rainy season. Oil SC formulations which have proved themselves in this context are, for example, those with the active ingredient mancozeb.

Commercially available oil SC formulations with the active ingredient mancozeb are, for example, Dithane 35 SC, Ridodur 35 SC (product of Laquinsa), Vondozeb 35 SC (product of Elf Atochem). Formulations of this type frequently comprise, as dispersant, an oil-soluble polymer, see U.S. Pat. Nos. 3,131,119, 3,773,976 and EP-A 875 142. EP-A 245 970 discloses the use of water-soluble, nonionic polymers to improve the rainfastness of the formulations.

However, storage stability is still unsatisfactory, even with these formulations. This applies in particular if the less stable active ingredient metiram, which comprises Zn as metal ion, is to be employed in place of the active ingredients mancozeb or Maneb, which are relatively stable. This is why liquid formulations with this active ingredient have not been disclosed as yet. However, metiram/oil SC formulations would be advantageous over mancozeb, owing to the higher zinc content of metiram, since it is known that even simple zinc salts already have a fungicidal, or biocidal, action.

On the other hand, the known liquid EBTC/oil SC formulations have even more disadvantages. Firstly, their active ingredient component is lower compared with the solid products. This is because, in oil SC formulations, sufficiently low viscosities are generally achieved when the solid component amounts to less than 40%. If not, there is a danger of the products no longer being sufficiently flowable because of unduly high viscosity.

A further disadvantage of the existing oil SC formulations, in particular oil SC formulations with active ingredients from the class of the EBTCs, is that such formulations frequently only have unsatisfactory rheological properties after storage. Thus, storage at elevated temperatures frequently leads to agglomeration effects, lump formation or pronounced settling of the solid phase. In some cases, the effects are even irreversible, i.e. even renewed shearing, for example by stirring, cannot rehomogenize the formulations.

It is an object of the present invention to provide essentially anhydrous liquid formulations with an active ingredient from the class of the dithiocarbamates, in particular metiram-comprising liquid formulations, which exhibit a high active ingredient content per liter, a low viscosity and high storage stability. It is also an object of the present invention to provide a process for the preparation of such essentially anhydrous liquid formulations.

We have found that this object is achieved in a first aspect of the invention by an essentially anhydrous liquid formulation comprising:

a) 10 to 70% by weight, preferably 30 to 60% by weight, of at least one active ingredient from the class of the dithiocarbamates, b) 10 to 89% by weight, preferably 20 to 60% by weight, of the abovementioned essentially anhydrous oil phase, c) 1 to 40% by weight, preferably 5 to 20% by weight, of a product selected from polyhydroxystearic acid, a derivative thereof, an alkyl or alkenyl polyether alkoxylate or a mixture thereof, d) 0 to 40% by weight, preferably 0 to 10% by weight of at lest one anionic surfactant, (in each case based on the total weight of the formulation).

A second aspect of the invention provides an essentially anhydrous liquid formulation comprising:

a) 10 to 70% by weight, preferably 30 to 60% by weight, of at least one active ingredient of the formula I hereinbelow

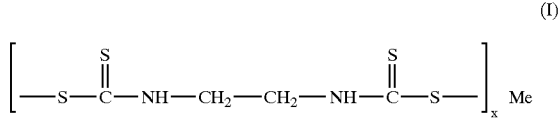

(I)

in which Me=Zn, $1 \leq x \leq 5$, b) 10 to 85% by weight, preferably 20 to 60% by weight, of an essentially anhydrous oil phase, c) 5 to 40% by weight, preferably 7.5 to 25% by weight, of at least one anionic surfactant, (in each case based on the total weight of the formulation).

In the abovementioned liquid formulation, the value for x is, in particular, in a range of 3 to 4.

Liquid formulation of the first aspect of the invention:

The dithiocarbamate active ingredients thus include the thiuram sulfides. Preferred active ingredients are ziram (zinc dimethyldithiocarbamate), thiram (tetramethylthiuram disulfide) and metham (sodium methyldithiocarbamate). Other preferred compounds are those of the formula (II),

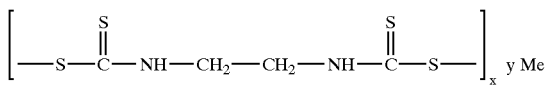

(II)

in which:

Me is a mono- or divalent agriculturally utilizable metal ion, in particular selected from amongst Zn, Mn, Na, Mg, Ca and/or K, preferably Zn and/or Mn, and $1 \leq x \leq 4$, preferably $3 \leq x \leq 4$, and y is 1 or 2, depending on the valence of Me.

These active ingredients are, in particular, maneb (manganese ethylenebisdithiocarbamate), mancozeb (the coordination product of maneb with zinc ions), nabam (sodium ethylenebisdithiocarbamate), zineb (zinc ethylenebisdithiocarbamate) and, preferably, metiram (compound of the formula I where x=3). Component b) is preferably an aprotic solvent, in particular at least one of the following components:

ba) a $C_8$- to $C_{30}$-hydrocarbon of the n- or iso-alkane series or a mixture thereof. Examples of such hydrocarbons are n- and iso-octane, -decane, -hexadecane, -octadecane, -eicosane, and preferably hydrocarbon mixtures such as liquid paraffin (which, in technical-grade quality can contain up to approximately 5% of aromatics), and a $C_{18}$–$C_{24}$-mixture which is commercially available from Exxon under the name Spraytex oil.

bb) aromatic or cycloaliphatic $C_7$- to $C_{18}$-hydrocarbon compounds, or a mixture thereof. These include, in particular, aromatic or cycloaliphatic solvents from the series of the alkyl-aromatics; the compounds can be unhydrogenated, partially hydrogenated or fully hydrogenated. Such solvents of component bb) include, in particular, mono-, di- or trialkylbenzenes, mono-, di-, trialkyl-substituted tetralins and/or mono-, di-, tri- or tetraalkyl-substituted naphthalenes (alkyl preferably represents $C_1$–$C_6$-alkyl). Examples of such solvents are toluene, o-, m-, p-xylene, ethylbenzene, isopropylbenzene, tert-butylbenzene and mixtures such as the Exxon products sold under the names Shellsol and Solvesso, for example Solvesso 100, 150 and 200.

bc) an aliphatic ester which is selected in particular from the group consisting of aliphatic esters, aralphatic esters and natural fats and oils and derivatives and mixtures thereof. Suitable substances are esters of aliphatic, saturated or unsaturated $C_1$–$C_{20}$-mono- and $C_2$–$C_{20}$-dicarboxylic acids with $C_1$–$C_{20}$-alkanols and phenyl-$C_1$–$C_{20}$-alkanols, the total of the carbon atoms being at least 8. Also suitable are esters of aromatic mono- or dicarboxylic acids, such as benzoic acid and phthalic acid, with $C_1$–$C_{20}$-alkanols and phenyl-$C_1$–$C_{20}$-alkanols. Preferred are methyl oleate, di-n-octyl and isooctyl adipate, octyl laurate, 2-ethylhexyl 2-ethylhexanoate, methyl oleate, n-butyl stearate, di-n-butyl adipate, di-n-nonyl and isononyl adipate, rapeseed oil methyl and ethyl esters, n-butyl benzoate, benzyl benzoate and the like.

The abovementioned fats or oils or derivatives which are of natural origin or have been left in their natural state (modified natural fats or oils) include, for example, substances such as soya oil, sunflower oil, rapeseed oil, corn oil and their raffination products.

The preferred component c) is polyhydroxystearic acid, particularly preferably polyhydroxystearic acid with 2 to 10, especially preferably 3 to 6, monomer units. An example is Solsperse 3000, which is commercially available (ICI).

Preferred polyhydroxystearic acid derivatives are reaction products of amines. Such amines include primary and/or secondary, linear $C_1$- to $C_{20}$ alkylamines and/or branched $C_3$- to $C_{20}$-alkylamines, or else they may be mono- or dialkylaminoalkylenedioligo- or -polyamines, it being possible for the alkylene group to have 2 to 4 carbon atoms and for the alkyl group to have 1 to 4 carbon atoms.

Examples are ethylenediamine, N,N-diethylenetriamine, triethylenetetramine, N,N-dimethylaminoethylamine, N,N-dimethylaminodiethylenetriamine, N,N-dimethylaminopropylamine, N,N-dimethylaminodipropylenetriamine and polyethyleneimines with a molecular weight of over 500, which may exhibit a low or high degree of branching.

The molar ratio of free acid function of the polyhydroxystearic acid to amine is especially preferably 1:5 to 10:1, in particular 1:1 to 5:1.

The reaction products of the polyhydroxystearic acid can also have cationic character, owing to quaternary nitrogen atoms. Substances which are suitable for quaternizing the nitrogen atoms are, for example, alkyl halides or alkyl sulfates, such as dimethyl sulfate.

Especially preferred are the reaction products of polyhydroxystearic acid with dimethylaminopropylamine, dimethylaminoethylamine and/or polyethyleneimine and the quaternization products thereof, for example the products quaternized with dimethyl sulfate. Examples are the commercially available Solsperse brands (ICI), in particular Solsperse 9.000, 13.000 and 17.000.

The alkyl or alkenyl radical in the alkyl- or alkenyl polyol ether alkoxylates can be straight-chain or branched and generally have 6 to 30 carbon atoms. The alkenyl radical can have one or more double bonds.

The preferred alkyl or alkenyl polyol ether alkoxylates can be obtained by reacting an alcohol with a chain length of 6 to 30, in particular 8 to 22, carbon atoms, which can be straight-chain or branched and can exist with or without double bonds, with epichlorohydrin and subsequently with a polyhydric alcohol such as, preferably neopentyl glycol or glycerin, and then alkoxylating the product with 1 to 20 mol of ethylene oxide (EO), propylene oxide (PO), butylene oxide (BO) or pentylene oxide.

When preparing the alkyl or alkenyl polyol ether alkoxylates, the components can be employed in any desired ratio. Preferred are alkyl glycidol ethers with chain lengths of $C_{12}$–$C_{18}$, reacted with polyhydric alcohols such as glycerin or neopentyl glycol in a ratio of 2:1 to 1:3, either unethoxylated or ethoxylated with 1 to 20 mol EO. very especially preferred are reaction products of alkyl glycidol ethers with chain lengths of $C_{16}$–$C_{18}$ which are reacted with glycerin and/or neopentyl glycol in a ratio of 1:1 to 1:2 and, if desired, subsequently ethoxylated with 0 to 5 EO units.

A typical representative of the class of the fatty alkyl glycerin ether ethoxylates is Cremophor WO CE 5115 (CAS-No.: 104376-61-6); a product of BASF AG).

If present, the surfactants d) amount to 0.1 to 40% by weight, in particular 5 to 10% by weight.

Useful anionic surfactants d) are soaps (alkali metal/alkaline earth metal/ammonium salts of the fatty acids), for example potassium stearate, alkyl sulfates and their mixtures, alkyl ether sulfates, alkylsulfonates, alkali metal, alkaline earth metal and ammonium salts of arylsulfonic acids and of alkyl-substituted arylsulfonic acids, alkylbenzenesulfonic acids such as, for example, lignin-, phenolsulfonic acid, naphthalene- and dibutylnaphthalenesulfonic acid, or dodecylbenzenesulfonates, alkylnaphthalenesulfonates, alkyl methyl ester sulfonates, acyl glutamates, mono- or dialkylsuccinic ester sulfonates, for example sodium di-isooctylsuccinic ester sulfonate, alkyl mono/diphosphates, sarcosinates, for example sodium lauroylsarcosinate, taurinates.

The anionic surfactants furthermore include condensates of sulfonated naphthalene and derivatives thereof with formaldehyde, condensates of naphthalenesulfonic acids, phenol and/or phenolsulfonic acids with formaldehyde or with formaldehyde and urea.

The sulfate and sulfonate surfactants are preferred. Component d) is especially preferably selected from:

da) alkyl sulfates, alkylsulfonates, alkylbenzene sulfates, alkylarylsulfonates, alkylpolyethoxysulfates, alkylphenol polyethoxysulfates and α-olefinsulfonates. The alkyl or α-olefin radical has, in particular, 6 to 30, preferably 8 to 22, carbon atoms. The number of ethoxy units is generally in the range of 1 to 50, preferably 1 to 25. The aryl radical is phenyl or a naphthyl radical which is substituted by one, two or three straight-chain or, in particular, branched $C_1$–$C_{12}$-alkyl radicals. The associated cation is an agriculturally utilizable mono- or divalent cation which is preferably selected from Na, Ca, K, Mg and $NH_4$. Examples of the surfactants da) are sodium lauryl sulfate, sodium lauryl ether sulfate, nonylphenol polyethoxysulfate, sodium diisobutylnaphthylsulfonate, and the like;

db) compounds from the group of the mono- and/or di-$C_6$–$C_{30}$-alkyl ester sulfosuccinates, where the cation is an agriculturally utilizable mono- or divalent cation, preferably selected from Na, Ca, K, Mg, Mn, Zn and NH4. Sodium dioctylsulfosuccinate is preferred; and/or dc) the anionic polymers of the subsequent formula (III)

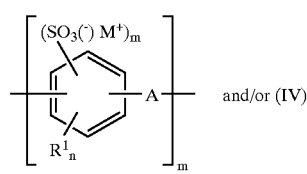

(III)

and/or (IV)

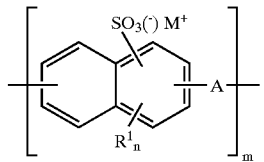

(IV)

in which M is an agriculturally utilizable mono- or divalent cation, preferably Na, Ca, K, Mg or $NH_4$, m is 0 or 1, n is an integer in the range $0 \leq n \leq 4$, m is an integer in the range $10^2 \leq m \leq 10^5$, $R^1$ is a $C_1$- to $C_8$-alkyl radical or hydroxyl radical and A a group selected from amongst methylene, 1,1-ethylene,

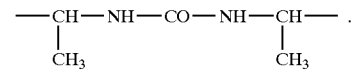

Products of the formulae III and IV are commercially available from BASF AG under the name Wettol or Tamol.

Liquid formulation of the second aspect of the invention:

The composition of the essentially anhydrous oil phase corresponds to that of the first aspect of the invention [component b)].

The surfactants c) correspond to those of the first aspect of the invention (component d)).

Auxiliaries contained in the formulations:

The formulations of both the first aspect of the invention and the second aspect of the invention may comprise auxiliaries. If present, then they are present in concentrations of 0.1 to 25% by weight, preferably 0.5 to 15% by weight, based on the total weight of the formulation. The auxiliaries may be further anionic components and/or cationic, zwitterionic or nonionic surfactants, or anionic, cationic or nonionic polymers.

Examples of anionic components are protein hydrolysates and, in particular, lignin-sulfite waste liquors and methylcellulose (dispersants).

The cationic surfactants which may be used include alkyltrimethylammonium halides, alkylpyridinium halides, and dialkyldimethylammonium halides.

The nonionic surfactants include fatty alcohol polyoxyethylene esters, for example lauryl alcohol polyoxyethylene ether acetate, or alkenyl alkoxylated animal and/or vegetable fats and/or oils, for example corn oil ethoxylates, castor oil ethoxylates, tallow fat ethoxylates, glycerin esters, such as, for example, glycerin monostearate, fatty alcohol alkoxylates and oxoalcohol alkoxylates of the type RO-$(R_1O)_x(R_2O)_yR_3$ in which $R_1$ and $R_2$ independently of one another=$C_2H_4$, $C_3H_6$, $C_4H_8$ and $R_3$=H, or $C_1$–$C_{12}$-alkyl, R=$C_3$–$C_{30}$-alkyl or $C_6$–$C_{30}$-alkenyl, x and y independently of one another are 0 to 50, it not being possible for both to be 0, such as iso-tridecyl alcohol and oleyl alcohol polyoxyethylene ether, fatty acid alkoxylates such as, for example, oleic acid ethoxylates, alkylphenol alkoxylates such as, for example, ethoxylated iso-octyl-, octyl- or nonylphenol, tributylphenol polyoxyethylene ether, fatty amine alkoxylates, fatty acid amide alkoxylates and fatty acid diethanolamide alkoxylates, in particular their ethoxylates, sugar surfactants, sorbitol esters such as, for example, sorbitan fatty acid esters (sorbitan monooleate, sorbitan tristearate), polyoxyethylene sorbitan fatty acid esters, alkyl polyglycosides, N-alkylgluconamides, alkylmethyl sulfoxides, alkyldimethylphosphine oxides such as, for example, tetradecyldimethylphosphine oxide.

The zwitterionic surfactants include sulfobetaines, carboxybetaines, alkyldimethylamine oxides such as, for example, tetradecyldimethylamine oxide.

Polymer surfactants which can be employed as auxiliaries to be used are, for example, di-, tri- and multi-block copolymers of the type (AB)x-, ABA, BAB, such as, for example, polyethylene oxide block polypropylene oxide block polyethylene oxide, polystyrene block polyethylene oxide, AB-comb polymers such as, for example, poly(meth)acrylate comb polyethylene oxide.

Other surfactants which can be employed, for example, are perfluoro surfactants, silicone surfactants, phospholipids such as, for example, lecithin or chemically modified lecithins, aminoacid surfactants such as, for example, N-lauroylglutamate.

Moreover, surface-active homo- and copolymers may also be employed in the liquid formulations according to the invention as auxiliaries: these include, for example, polyvinylpyrrolidone, polyacrylic acid, polyvinyl alcohol, polypropylene oxide, polyethylene oxide, maleic anhydride/isobutene copolymers, vinylpyrrolidone/vinyl acetate copolymers.

The alkyl chains of the abovementioned auxiliaries can be linear or branched. The alkyl chain lengths are, in general, between 8 and 22 carbon atoms.

Frequently, mixtures of the surfactants are particularly suitable. The auxiliaries mentioned can be added before or after grinding to the aqueous dithiocarbamate or EBDC SC intermediate product or to the oil SC batch to be formulated.

To widen the spectrum of action and to achieve synergistic effects, liquid formulations may be applied in accordance with the invention as a mixture with a large number of representatives of other groups of fungicidal active ingredients, and, accordingly, also jointly. Suitable components in mixtures are, for example: morpholine compounds such as tridemorph, fenpropimorph, fenpropidin and spiroxamin; strobilurins such as azoxystrobin, kresoxim methyl; triazoles such as tebuconazole, flusilazole, propiconazole, fenbuconazole; epoxiconazole; benzimidazoles such as carbendazim, benomyl; valinamides such as sprovalicarb or KIF 230 by Kumiai; thiophanates, such as thiophanate-methyl, and also chlorothalonil. These active ingredients can be incorporated into the formulations according to the invention or added to the spray mixture.

The formulation of the first aspect of the invention can also be mixed with the other active ingredients, which are encompassed by the formulation of the second aspect of the invention.

Also of interest is the miscibility with mineral salt solutions which are employed for remedying nutritional and trace element deficiencies. Nonphytotoxic oils and oil concentrates and antidrift reagents may also be added.

The formulations according to the invention are preferably prepared in a method in which a highly-concentrated (approx. 30 to 60% by weight active ingredient), aqueous microparticulate dispersion of the active ingredient, for example of the active ingredient metiram, is first prepared by grinding in the presence of at least one nonionic or anionic surfactant (for example component d) of the first aspect or component c) of the second aspect) and subsequently spray-dried. If the grinding step involves an anionic surfactant d) or c), all or some of the intended quantity can be employed during the grinding step.

To prepare the formulation of the first aspect of the invention, the powder or granules obtained after spray-drying is or are ground or processed with the oil component b), the component c) and, if appropriate, the rest or all of the anionic surfactant and, if appropriate, other auxiliaries and/or additives.

To prepare the formulation of the second aspect of the invention, the powder or granules is or are ground or processed in a similar manner with the oil component b) and the remainder or all of the anionic surfactant c) and, if appropriate other auxiliaries and/or additives.

The measures and apparatus required for the preparation are known to those skilled in the art.

It is particularly advantageous to stabilize the formulations according to the invention. This is effected by adding 1 to 5% by weight of a stabilizer (based on the active ingredient content) to an aqueous, technical-grade preconcentrate of the active ingredient prior to spray-drying.

The stabilizer is either added during the preparation of the aqueous SCs, i.e. while the technical-grade active ingredient is ground, or after grinding, but before the step in which the material is spray-dried to give the DF (dry flowable) intermediate product.

Preferred stabilizers are formaldehyde, paraformaldehyde or urotropin.

The additional stabilization with formaldehyde is carried out essentially in agreement with the known prior art, see DE-A 33 38 979.

Other stabilizers which are suitable are—as has already been mentioned above in some cases—HMS, calcium salts, for example calcium oxide or calcium carbonate, see EP-A-568 378 and 460 612.

Thickeners which the oil SC formulations according to the invention may furthermore comprise are mineral constituents such as, for example, bentonites, talcites or hectorites, by means of which the physical properties of the formulations with regard to less serum formation or less sedimentation can generally be improved.

Furthermore, such additions can also suppress chemical processes which take place in the formulations upon storage, in most cases as a consequence of an increased viscosity, which may lead to an improved stability of the active ingredient. Other organic thickeners which may be suitable are, for example, castor oil derivatives.

The liquid formulations according to the invention constitute a concentrate which comprises the active ingredient with a medium particle size in the range of 0.1 to 10 μm, preferably 0.5 to 5 μm. For use as crop protection product in agriculture (in particular for banana and coffee plantations), the concentrate is converted into a form which is suitable for application by diluting it in the customary manner prior to use. In particular, the use in the form of a spray mixture preparation is particularly preferred.

The fact that a virtually anhydrous oil-based formulation is present also allows application by the ULV method (ultra-low volume), for example by aerial application.

For a customary tankmix spray mixture, 0.5 to 10, preferably 1 to 5, l/ha of the formulation according to the invention are diluted with water to 5 to 2,000 l. For a ULV tankmix spray mixture, 0.5 to 10 l, preferably 1 to 5 l/ha of the formulation according to the invention are diluted to 5 to 50 l with an oil phase, preferably an oil of component b), or with water or a mixture of water and oil in a ratio of approximately 2:1 to 4:1 by volume. If appropriate, 0.1% to 5% by weight (based on the spray mixture) of other anionic, cationic or nonionic surfactants, auxiliaries, polymers and/or of the abovementioned other fungicidal active ingredients are added to the tankmix mixture. Substances which are examples of such, surfactants and other auxiliaries have already been described above. Substances which must be mentioned in particular are starch and starch derivatives, for example a starch comprising carboxyl and sulfonyl groups (Nu-Film by Union Carbide Corp.) and spreaders and extenders such as Vapor Guard by Miller Chemical & Fertilizer Corp.

The invention is illustrated in greater detail by the examples which follow:

TABLE 1

Auxiliaries and active ingredients used in the examples

| Name | Structural type/active material | Manufacturer |
| --- | --- | --- |
| Lutensol TO 3 | $C_{13}$-oxoalcohol × 3 EO | BASF |
| Glycerox HE | Polyoxyethylene coconut fatty acid glycerin ester | Croda |
| Glycerox L 8 | Glycerin monolaurate × 8 EO | Croda |
| Alkamuls T/80 | Polyoxyethylene sorbitan mono-oleate | Rhodia |
| Emulan ELP | Castor oil × 11 EO | BASF |
| Emulan EL 36 | Castor oil × 36 EO | BASF |
| Emulan A | Oleic acid × 5.5 EO | BASF |
| Solutol HS 15 | 12-Hydroxystearic acid × 15 EO | BASF |
| Atlas G 1086 | Polyoxyethylenesorbitol heptaisostearate | Uniqema |
| Atlas G 1049 | Polyoxyethylenesorbitol hexaoleate | Uniqema |
| Wettol NT 1 | sodium diisobutylnaphthyl-sulfonate | BASF |
| Solsperse 3.000 | Polyhydroxystearic acid (PHS) | ICI |
| Solsperse 9.000 | PHS + dimethylaminoethylamine | ICI |
| Cremophor WO CE 5115 | Oleylglycerin ether ethoxylate | BASF |
| Spraytex-01 | $C_{18}$–$C_{24}$-hydrocarbon mixture | Exxon |
| Dithane | Manganese ethylenebis (dithiocarbamate) complex with zinc salt (mancozeb) | Rohm & Haas |
| Dithane OS | Mancozeb oil SC based on at least 10% by weight of liquid paraffin | Rohm & Haas |
| Metiram | Compounds of the formula I where x = 3 | BASF |
| Vondozeb 33 OF | Mancozeb | Elf Atochem |
| Aerosol OT-A Surfactant | dioctyl sulfosuccinate in petroleum distillate | Cytec Industries |

PREPARATION EXAMPLES

When carrying out the examples given herein, the technical-grade active ingredients used in accordance with the invention were first ground with auxiliary in the presence of water. The resulting aqueous Scs (suspension concentrates) were subsequently spray dried and, in a third step, ground again with other auxiliaries in the absence of water to give the actual oil SCs.

However, the technical-grade active ingredient may also be freed from water by simple vacuum drying while heating the samples gently, optionally also under atmospheric pressure in a stream of air using warmed air or in a stream of nitrogen gas. The abovementioned spray-drying step is thus dispensed with.

The grinding medium[ ]used for aqueous or anhydrous SCs are made of glass or other minerals or metals and have a size of 0.1–30 mm, in particular 0.6–2 mm, and the suspension is generally comminuted until a mean particle size of well below 10 μm is achieved.

The grinding operation was generally carried out continuously, i.e. by constantly recirculating the SCs, or batchwise, i.e. by completely and repeatedly pumping through or passing through an oil SC batch.

Grinding was effected, for example, batchwise in a "Dynomühle" mill (Bachofen) with a batch size of 0.5 to 1 liter. After, in general, 5 passes (pumping the suspension through the mill with the aid of a hose pump), microscopic evaluation revealed mean particle sizes of 0.5 to 10 μm.

As shown in the formulas hereinbelow, other auxiliaries were then incorporated by homogenizing for 10 minutes with KPG or magnetic stirrers.

Preparation Example 1.1

Preparation protocol for a metiram DF as intermediate product for oil SC formulations Formula and amounts of ingredients used:

| Amount (g) | Ingredients |
| --- | --- |
| 736.00 | metiram filter cake, approx. content 41%, aqueous |
| 45.00 | Formaldehyde (purity 37%), aqueous |
| 37.50 | Wettol NT 1 |
| 85.71 | Water |

The metiram filter cake suspension was stirred vigorously for 30 minutes in a glass beaker at RT with 45 g of formaldehyde (purity 37%) and 37.5 g of Wettol NT1. An aqueous metiram SC was then prepared using a "Dynomühle" mill (equipped with 5 polymer disks and packed with 510 ml of glass beads (size 1.4–1.6 mm)) at 20° C. with water-cooling in 5 passes, while monitoring the temperature.

The yellow, slightly viscous product is dried for 4 days at 40° C. in a vacuum drying oven (8 mbar).

Alternatively, comparatively larger batches were dehydrated by spray-drying at an input temperature of 160° C.–180° C. and an output temperature of 90° C.

Analytical data:

a.i. (active ingredient) content: 85.98%

ETU (ethylenethiourea) content: 0.06%

Product: finely divided, homogeneous yellow powder

Water content:<0.6% by weight

Preparation Example 1.2

Preparation of a Metiram Oil SC

Formula and Amounts of Ingredients Used

| Amount (g) | Ingredients |
| --- | --- |
| 465 | metiram DF intermediate product of Example 1.1 |
| 50 | Solsperse 3000 |
| 459.9 (to 1 l) | liquid paraffin |

465 g of metiram.DF intermediate product of Example 1.1 were stirred into a mixture of 459.9 g of liquid paraffin and 50 g of Solsperse 3000 by means of dissolvers. The viscous suspension was ground in the "Dynomühle" mill of Example 1.1 at not more than 20° C. in 5 passes with cooling to a particle size of ≦2 μm (content>40%).

Product: a slightly viscous oil SC with 400 g/l a.i. metiram. The oil SC variants given in Table 3 are obtained in a similar manner.

Example 1

Viscosity of EBDC oil SC formulations with mancozeb active ingredient. The composition of the formulations and the results are shown in Table 2.

TABLE 2

| Experiment | Ingredients 95% Dithane OS + auxiliary (percentage) | | Viscosity (mPa · s) |
|---|---|---|---|
| Comparison | Spraytex oil | 5 | 205 |
| Comparison | w/o add. 100% Dithane OS | | 224 |
| according to the invention | Solsperse 3000 | 5.0 | 373 |
| according to the invention | Solsperse 9000 | 5.0 | 159 |
| according to the invention | Cremophor WO CE 5115 | 5.0 | 160 |
| | Cremophor WO CE 5115 and Solsperse 3000 | 2.5 2.5 | 261 |

Example 2

The storage stability of the metiram oil SC formulations shown in Table 3 was determined. The results are also shown in Table 3.

TABLE 3

Metiram oil SC formulations

| Assessment after storage for 4 weeks, 40° C. | Formula | Stability (active ingredient) | Solvent to 1 l |
|---|---|---|---|
| I:S | 400 g/l metiram 50 g Cremophor WO CE 5115 50 g Wettol NT 1 | 96.7% | Spraytex oil |
| I:S,R | 400 g/l metiram 50 g Solsperse 3000 50 g Wettol NT 1 | 94.8% | liquid paraffin |
| I:S,R | 400 g/l metiram 50 g Solsperse 9000 50 g Wettol NT 1 | 95.7% | liquid paraffin |
| I:S,R | 500 g/l metiram 50 g Solsperse 9000 50 g Wettol NT 1 | 96.6% | liquid paraffin |
| I:S,R | 500 g/l metiram 50 g Solsperse 9000 50 g Wettol NT 1 | 96% | liquid paraffin |
| I:S,R | 400 g/l metiram 50 g Solsperse 9000 100 g Wettol NT 1 | 96% | liquid paraffin |
| I:S,R+ | 400 g/l metiram 100 g Solsperse 9000 50 g Wettol NT 1 | 94.9% | liquid parafiin |
| C:U,L | 400 g/l metiram 50 g Alkamuls T/80 50 g Wettol NT 1 | ndg | liquid paraffin |
| C:U,L | 400 g/l metiram 50 g Solutol HS 15 50 g Wettol NT 1 | ndg | liquid paraffin |
| C:U,L | 400 g/l metiram 50 g Emulan A 50 g Wettol NT 1 | ndg | Spraytex oil |
| C:U,L | 400 g/l metiram 50 g Atlas G 1086 50 g wettol NT 1 | ndg | Spraytex oil |

TABLE 3-continued

Metiram oil SC formulations

| Assessment after storage for 4 weeks, 40° C. | Formula | Stability (active ingredient) | Solvent to 1 l |
|---|---|---|---|
| C:U,L | 400 g/l metiram 50 g Atlas G 1049 50 g Wettol NT 1 | ndg | Spraytex oil |
| C:I,L | 400 g/l metiram 50 g Lutensol TO3 50 g Wettol NT 1 | ndg | Spraytex oil |
| C:U,L | 400 g/l metiram 50 g Glycerox HE 50 g Wettol NT 1 | ndg | Spraytex oil |
| C:U,L | 400 g/l metiram 50 g Glycerox L8 50 g Wettol NT 1 | ndg | Spraytex oil |
| C:U,L | 400 g/l metiram 50 g Emulan EL 36 50 g Wettol NT 1 | ndg | Spraytex oil |
| C:U,L | 400 g/l metiram 50 g Emulan ELP 50 g Wettol NT 1 | ndg | Spraytex oil |

Explanations of the rheological assessment after 4 weeks at 40° C.:

C=Comparative experiment with:
(U=unstable/unsuitable; L=irreversible lumps/agglomeration).

I=Formulation according to the invention with:
(expressed in Table 3 as active ingredient content after storage based on active ingredient content before storage) (S=improved stability of the active ingredient, R=improved rheology/viscosity, or relatively good thixotropy, R+: very low viscosity, best properties)

n.d.=data not determined, in general owing to the evolution of gas (g) or unsuitable rheological properties.

The comparative experiments demonstrate that the formulations are unstable and that lumps or agglomerates are formed. In some cases, the effects occur as early as after a few days.

In contrast, the formulations according to the invention were homogeneous even after four weeks of storage and the activity of the active ingredient is essentially retained.

Example 3

A metiram oil SC was prepared from the following ingredients in accordance with the Preparation Examples 1.1 and 1.2:

| | |
|---|---|
| metiram | 400 g |
| Wettol NT 1 | 50 g |
| Aerosol OT-A Surfactant | 300 g |
| Liquid paraffin to | 1,000 ml |

The resulting oil SC showed low viscosity and was well suited for the preparation of tankmix spray mixtures.

We claim:

1. An essentially anhydrous dithiocarbamate liquid formulation comprising:
   a) 10 to 70% by weight of at least one active ingredient from the class of the dithiocarbamates,
   b) 10 to 89% by weight of an essentially anhydrous oil phase, c) 1 to 40% by weight of polyhydroxystearic acid or a derivative thereof and/or an alkyl or alkenyl polyol ether alkoxylate, d) 0 to 40% by weight of at least one anionic surfactant.

2. A liquid formulation as claimed in claim 1, where the dithiocarbamate is selected from the group consisting of ziram, tiram, nabam, metham and the compounds of the formula II hereinbelow

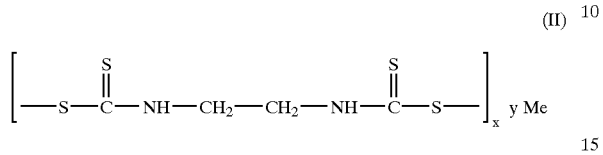

in which:

Me is a mono- or divalent agriculturally utilizable metal ion, $1 \leq x \leq 4$, and y, depending on the valence of Me, is 1 or 2.

3. A liquid formulation as claimed in claim 1, where the active ingredient is selected from mancozeb and metiram.

4. A liquid formulation as claimed in claim 1, wherein component b) comprises at least one of the following components:

ba) a $C_8$- to $C_{30}$-hydrocarbon of the n- or iso-alkane series or a mixture thereof, bb) an aromatic or cycloaliphatic $C_7$- to $C_{18}$-hydrocarbon or a mixture thereof, bc) an aliphatic ester selected from the group consisting of aliphatic dicarboxylic esters, aromatic esters, natural fats and oils and their derivatives and mixtures.

5. A liquid formulation as claimed in claim 4, where component bb) is selected from the group consisting of mono-, di-, trialkylbenzenes, mono-, di-, trialkyl-substituted tetralins and mono-, di-, trialkyl-substituted naphthalenes.

6. A liquid formulations as claimed in claim 4, where component bc) is selected from the group consisting of methyl oleate, dioctyl, adipate, octyl laurate, 2-ethylhexyl 2-ethylhexanoate and benzoic esters.

7. A liquid formulation as claimed in claim 1, where the hydroxystearic acid derivative is a reaction product of polyhydroxystearic acid with a polyethylene-imine or a mono- or di-$C_1$–$C_4$-alkylamino-$C_2$–$C_2$-alkyleneamine or a $C_1$–$C_4$-alkyl-quaternized product thereof.

8. A liquid formulation as claimed in claim 1, where the anionic surfactant d) is selected from da) the group consisting of alkyl sulfates, alkylsulfonates, alkylbenzene sulfates, alkylarylsulfonates, alkyl polyethoxysulfates, alkylphenol polyethoxysulfates and α-olefinsulfonates, the cation being an agriculturally utilizable mono- or divalent cation, db) compounds of the group of the mono- and/or di-$C_6$–$C_{30}$-alkyl ester sulfosuccinates, the cation being an agriculturally utilizable mono- or divalent cation, and/or dc) the anionic polymers of the subsequent formula (III)

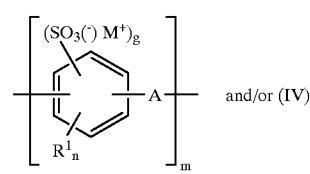 and/or (IV)

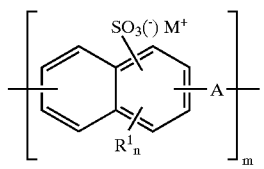

in which M is an agriculturally utilizable mono- or divalent cation g is 0 or 1, n is an integer in the range $0 \leq n \leq 4$, m is an integer in the range $100 \leq m \leq 10^5$, $R^1$ is $C_1$- to $C_8$-alkyl radical or hydroxyl radical and A is a methylene 1, 1-ethylene,

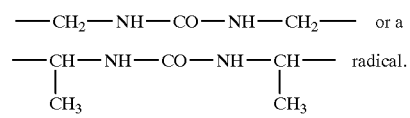

9. A liquid formulation as claimed in claim 8, where the anionic surfactant is an alkylarylsulfonate or an anionic polymer cc).

10. A liquid formulation as claimed in claim 1 comprising a) 10 to 70% by weight of an active ingredient of the formula I

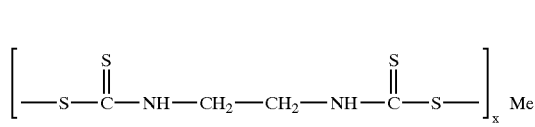

where Me-Zn, $1 \leq x \leq 5$, b) 10 to 89% by weight of a $C_8$–$C_{30}$-hydrocarbon or a mixture thereof, c) 1 to 40% by weight of polyhydroxystearic acid and/or a reaction product of polyhydroxystearic acid with a polyethyleneimine or a mono- or $_{di-C1}$-$C_4$-alkylamino-$C_2$-$C_2$-alkyleneamine or a $C_1$–$C_4$-alkyl-quaternized product thereof, and d) 0.5 to 20% by weight of an alkylarylsulfonate or an anionic polymer cc).

11. An essential anhydrous dithiocarbamate liquid formulation comprising:

a) 10 to 70% by weight of at least one active ingredient of the formula I hereinbelow

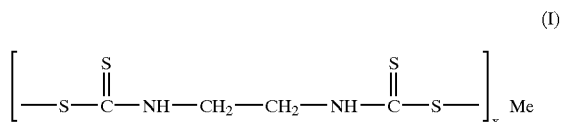

in which Me=Zn, $1 \leq x \leq 5$, b) 10 to 85% by weight of an essentially anhydrous oil phase, and c) 5 to 40% by weight of at least one anionic surfactant, where the anionic sufactant c) is selected from ca) the group consisting of alkyl sulfates, alkylsulfonates, alkylbenzene sulfates, alkylarylsulfonates, alkyl polyethoxysulfates, alkylphenol polyethoxysulfates and α-olefinsulfaonates, the cation being an agriculturally utilizable mono- or divalent cation, cb) compound of the gorup of the mono- and/or di-$C_6$–$C_{30}$-alkyl ester sulfosuccinates, the cation being an agriculturally utilizable mono- or divalent cation, and/or cc) the anionic polymers of the subsequent formula (III)

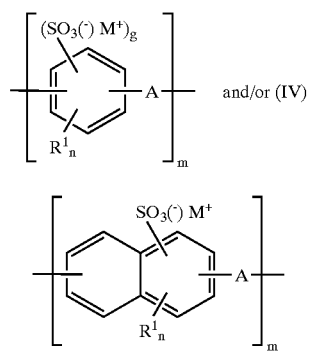

in which M is an agriculturally utilizable mono- or divalent cation, g is 0 or 1, n is an integer in the range $0 \leq n \leq 4$, m is an integer in the range $100° \leq m \leq 1o^5$, $R^1$ is a $C_1$- to $C_8$-alkyl radical or hydroxyl radical and A lis a methylene 1, 1-ethylene

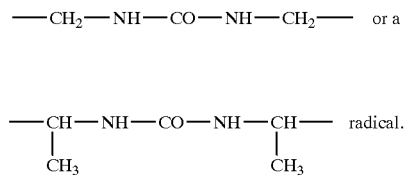

12. A liquid formulation as claimed in claim 11, where $3 \leq x \leq 4$.

13. A crop protection product suitable for aerial application which comprises a formulation as defined in claim 1.

* * * * *